United States Patent
Myers et al.

(10) Patent No.: US 11,457,109 B2
(45) Date of Patent: *Sep. 27, 2022

(54) RELATIONSHIP DETERMINATION SYSTEM

(71) Applicant: Express Scripts Strategic Development, Inc., St. Louis, MO (US)

(72) Inventors: Christopher M. Myers, Dublin, OH (US); Danielle L. Smith, Cedar Park, TX (US)

(73) Assignee: Express Scripts Strategie Development, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/338,873

(22) Filed: Jun. 4, 2021

(65) Prior Publication Data

US 2021/0297532 A1 Sep. 23, 2021

Related U.S. Application Data

(63) Continuation of application No. 16/440,357, filed on Jun. 13, 2019, now Pat. No. 11,039,014.

(51) Int. Cl.
*H04M 3/00* (2006.01)
*H04M 3/51* (2006.01)
(Continued)

(52) U.S. Cl.
CPC ........ *H04M 3/5191* (2013.01); *G06F 40/295* (2020.01); *G06N 3/049* (2013.01); *G10L 15/26* (2013.01); *G16H 10/60* (2018.01)

(58) Field of Classification Search
CPC .... H04M 3/5191; G16H 10/60; G06F 40/295; G06N 3/049; G10L 15/26
See application file for complete search history.

(56) References Cited

U.S. PATENT DOCUMENTS

| | | |
|---|---|---|
| 10,152,972 B1 | 12/2018 | Thomas et al. |
| 2014/0236626 A1 | 8/2014 | Reddy Bynagari |
| 2019/0014213 A1 | 1/2019 | Babjack |

FOREIGN PATENT DOCUMENTS

| | | |
|---|---|---|
| EP | 1979825 A1 | 10/2008 |
| EP | 3128442 A1 | 2/2017 |

(Continued)

*Primary Examiner* — Rasha S Al Aubaidi
(74) *Attorney, Agent, or Firm* — Schwegman Lundberg & Woessner

(57) ABSTRACT

A method starts with processor retrieving member's initial context data. Processor receives a string that is a transcribed utterance or an electronic message from the communication session established between member client device and agent client device. Processor determines potential relationships between the member and a patient that is the subject of the string by processing the string using Long Short-Term Memory (LSTM) neural networks to generate a plurality of relationship values. Relationship values are associated with relationship types. Processor generates weight values based on member's initial context data for each of the plurality of relationship types, and generates probability values for the relationship types based on the relationship values and the weight values. Processor narrows the potential relationships, generates relationship data that includes the narrowed potential relationships, and causes the relationship data to be displayed by the agent client device. Other embodiments are disclosed herein.

20 Claims, 7 Drawing Sheets

(51) Int. Cl.
    *G06N 3/04*     (2006.01)
    *G16H 10/60*     (2018.01)
    *G10L 15/26*     (2006.01)
    *G06F 40/295*     (2020.01)

(56) References Cited

FOREIGN PATENT DOCUMENTS

| | | | |
|---|---|---|---|
| EP | 3316139 | A1 | 5/2018 |
| WO | 199849612 | A1 | 11/1998 |
| WO | 2001074054 | A1 | 10/2001 |
| WO | 2017044118 | A1 | 3/2017 |
| WO | 2018005204 | A1 | 1/2018 |
| WO | 2018063553 | A1 | 4/2018 |

RELATIONSHIP DETERMINATION SYSTEM

CROSS-REFERENCE TO RELATED APPLICATIONS

This application is a continuation of U.S. application Ser. No. 16/440,357, which was filed Jun. 13, 2019. The entire disclosure of said application is incorporated herein by reference.

BACKGROUND

Since a user's perception of an organization can be greatly influenced by the customer service that is provided to the user, the organization has interest in ensuring that the user's experience with the customer service is impeccable. While, traditionally, customer service is a face-to-face interaction between the user and an agent that is employed by the organization, in order to increase the ability for the user to access to an agent of the organization, customer service is now accessible via many different means of communication. For example, a user may communicate with a human agent or an automated agent via an audio call (e.g., voice over IP (VoIP), telephone) or via an electronic messaging (e.g., online chat, text messaging).

Whether the user is interacting with a human agent or an automated agent, customer service aims to help the user complete his transaction in the most timely and efficient manner while ensuring that the user's experience with the customer service is enjoyable.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

Figure 1:
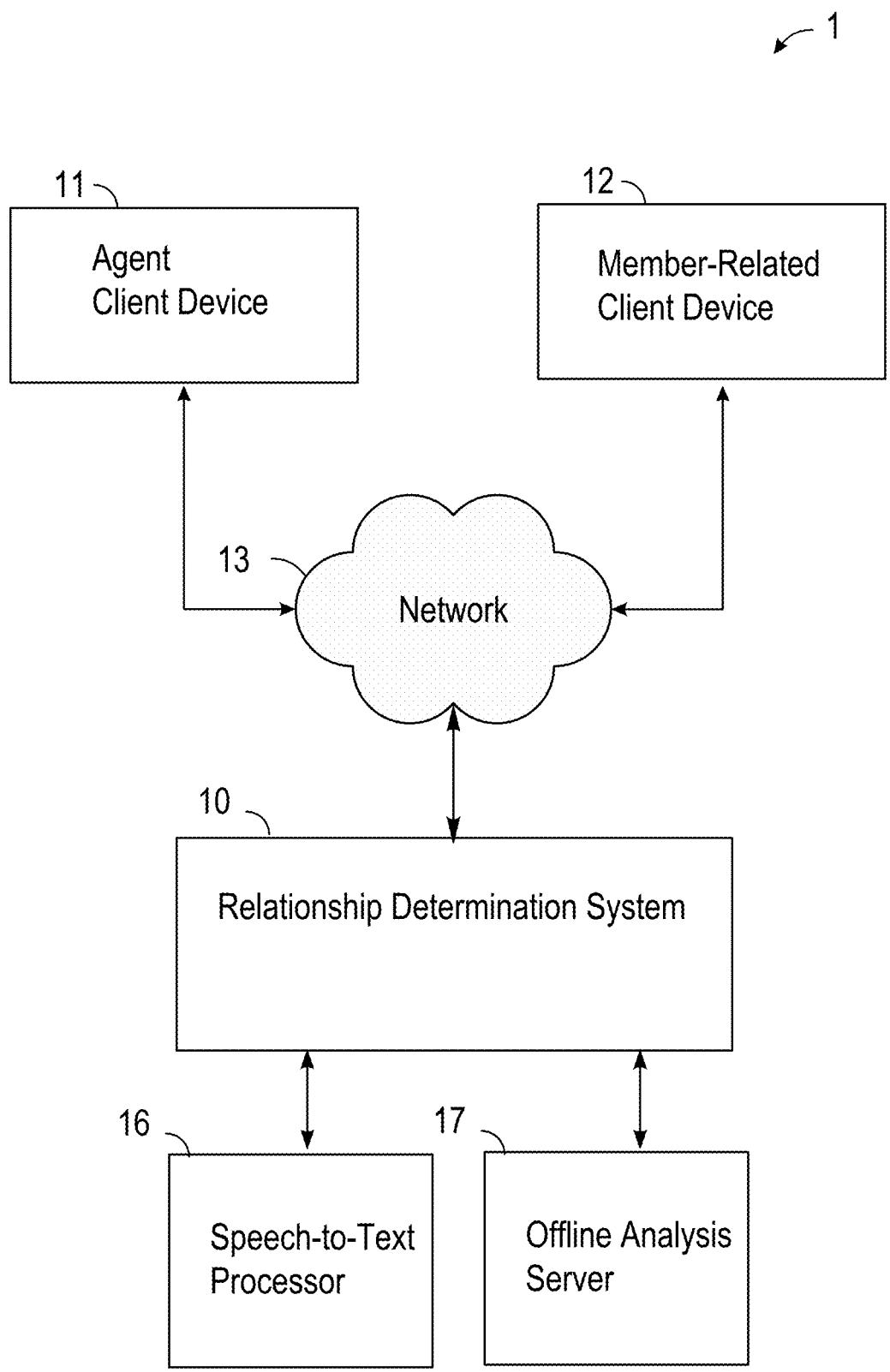
FIG. 1 is a block diagram showing an example system including a relationship determination system according to various exemplary embodiments.

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Among other things, embodiments of the present disclosure improve the functionality of customer service methods and systems. An organization can provide its members with access to customer service via an audio call (e.g., telephone call, VoIP, etc.) or via electronic messages (e.g., online chat, instant messaging, email, etc.). The customer service system maintains databases that store, for example, data on each member. Accordingly, when the member contacts the customer service, the customer service system identifies the member using the initial context data (e.g., the phone number the member is calling from, the website login information inputted, automatic number identification (ANI), etc.) and retrieves the data on the member (e.g., member account information, name, address, insurance information, information on spouse and dependents, etc.). However, a user can also contact customer service on behalf of someone else, e.g., a member. For example, when the service provided by the organization is medical in nature, customer service call centers can receive calls or electronic messages from a user who is a member regarding prescriptions for another patient such as the member's child, spouse, or parent. The user can also be a professional caregiver contacting the customer service on behalf of the patient, who is a member. Accordingly, to further improve the functionality of customer service software and systems, embodiment of the present disclosure determines the relationship between the user (e.g., another member, a caretaker, etc.) and the member on behalf of which the user is contacting customer service. Once the relationship is determined, the relationship can be communicated to the agent of the organization who can then streamline the process needed for the user to complete a task on behalf of this other person (e.g., a member).

A medical group may use the customer service methods and systems as described herein. A medical group may include members, people who benefit from the medical group or are provided with medical treatment by the group. The medical group can be a medical insurer. The medical group can be a pharmacy benefit manager (PBM). The PBM may store data regarding member usage of prescription drugs. This data may be leveraged in order to provide a member the benefit and may be paid for by a client of the of the PBM. The clients of the PBM can include employers, group purchasing organizations, and governmental groups. In general, prescription drug and medicine data may be accessed from a PBM database. One or more operations may be performed on the prescription drug and medicine data to generate relationship data between a member and a user contacting the medical group system as described herein. The user contacting the medical group system can include a person related to the patient, a guardian of the patient, a caregiver of the patient, a medical care provider of the patient. In some cases, the user is also a member and is contacting the medical group on behalf of another member.

FIG. 1 is a block diagram showing an example system 1 according to various exemplary embodiments. The system 1 can be a customer service system that includes a relationship determination system 10, an agent client device 11, and a member-related client device 12 that are communicatively coupled over a network 13 (e.g., Internet, telephony network). The agent client device 11 and the member-related client device 12 can be communicatively coupled via an audio call (e.g., VoIP, Public Switched Telephone Network, cellular communication network, etc.) or via electronic messages (e.g., online chat, instant messaging, text messaging, email, and the like). In another embodiment, the agent client device 11 and the member-related client device 12 are communicatively coupled via a telephone call using a telephony network, such as network 13. While FIG. 1 illustrates a single agent client device 11 and a single member-related client device 12, it is understood that a plurality of agent client devices 11 and a plurality of member-related client devices 12 can be included in the system 1 in other embodiments. As used herein, the term "client device" may refer to any machine that interfaces to a communications network (such as network 13) to obtain or to exchange resources from one or more server systems or other client devices. A client device may be, but is not limited to, a mobile phone, desktop computer, laptop, portable digital assistants (PDAs), smart phones, tablets, ultra books, netbooks, laptops, multi-processor systems, microprocessor-based or programmable consumer electronics, game consoles, set-top boxes, or any other communication device that a user may use to access a network.

The network 13 may include, or operate in conjunction with, an ad hoc network, an intranet, an extranet, a virtual private network (VPN), a local area network (LAN), a wireless network, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

In the example shown in FIG. 1, a user of the member-related client device 12 can establish a communication session with an agent associated with the agent client device 11. The agent can be a human agent or an automated agent. The automated agent can be an interactive voice response (IVR), a virtual online assistant, or a chatbot. The automated agent can be associated with a medical group that includes the member. During a communication session between the user and the agent, the relationship determination system 10 can analyze utterances or electronic messages from the communication session to build and transmit the relationship data to the agent client device 11 as it related to a specific individual member.

In FIG. 1, the system 1 can also include an offline analysis server 17 and a speech-to-text processor 18 that are communicatively coupled to each other and to the relationship determination system 10.

Figure 2:
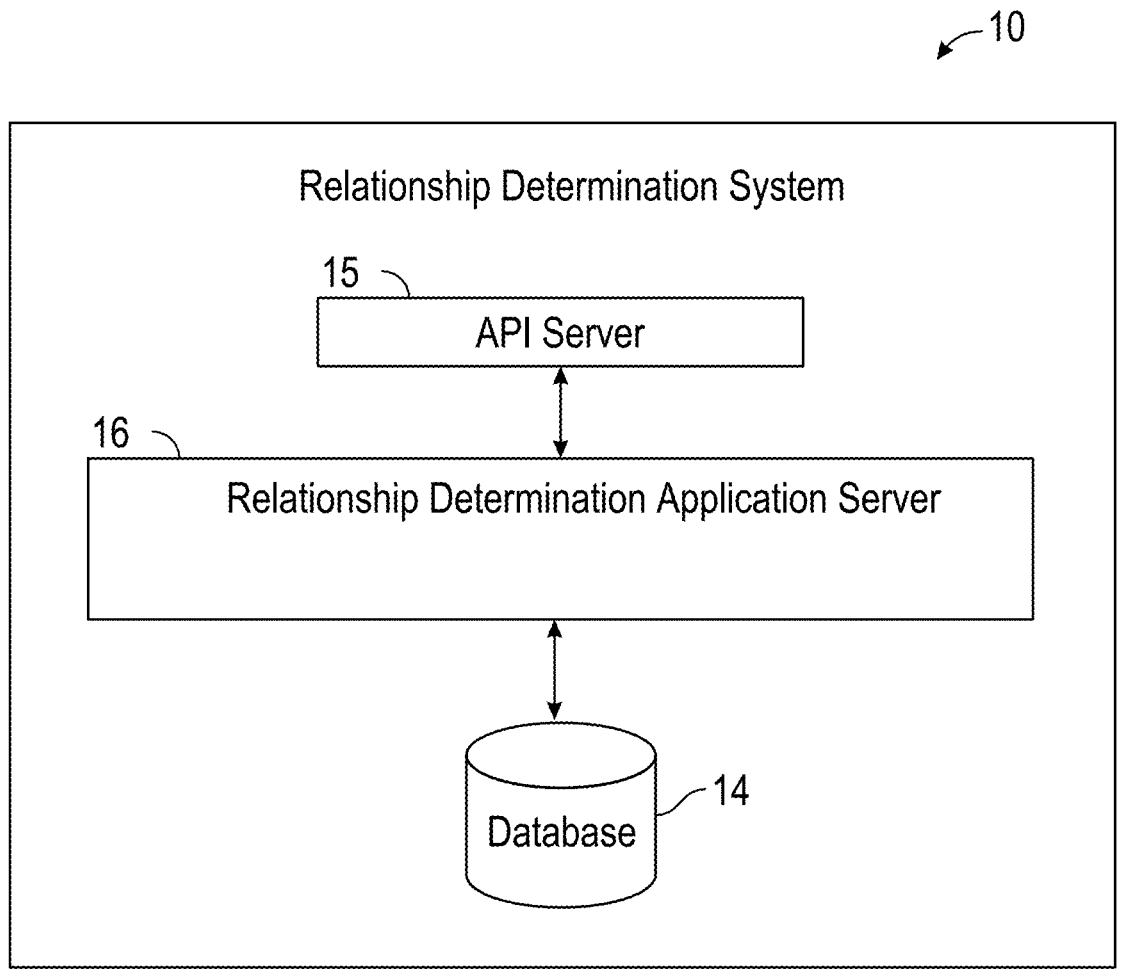
FIG. 2 is block diagram illustrating further details regarding the relationship determination system, according to exemplary embodiments.

FIG. 2 is block diagram illustrating further details regarding the relationship determination system 10, according to exemplary embodiments. The relationship determination system 10 includes an Application Program Interface (API) server 15 is coupled to, and provides a programmatic interface to, a relationship determination application server 16. For example, the relationship determination application server 16, using the API server 15, can create events based on the relationship data generated. The relationship determination application server 16 is communicatively coupled to the database 14, in which is stored data processed by the relationship determination application server 16 to build and transmit the relationship data, as further described herein.

The Application Program Interface (API) server 15 receives data (e.g., strings that are on the transcribed or digitized utterances or electronic messages) and transmits data (e.g., relationship data) between the agent client device 11 and the relationship determination application server 16. Strings that are on the transcribed or digitized utterances or electronic messages can be an array data structure of words comprising phrases of input from a user. The Application Program Interface (API) server 15 can receive and transmit data between the agent client device 11 and the relationship determination server 16 in real-time. Specifically, the Application Program Interface (API) server 15 provides a set of interfaces (e.g., routines and protocols) that can be called or queried by the relationship determination application server 16 in order to invoke functionality of the relationship determination system 10. In one embodiment, the Application Program Interface (API) server 15 can also receive data (e.g., strings that are on the transcribed/digitized utterances or electronic messages) from an offline analysis server 17 (in FIG. 1) that is performing offline analysis of call recordings or chat transcripts between the member-related client device 12 and the agent client device 11. In this embodiment, the Application Program Interface (API) server 15 can transmit data (e.g., relationship data) from the relationship determination application server 16 to the offline analysis server 17. When the communication session between the agent client device 11 and the member-related client device 12 is an audio communication (FIG. 1), a speech-to-text processor 18 (FIG. 1) can process the audio communication to convert each utterance from speech to text to generate the string that is received by the Application Program Interface (API) server 15. In some embodiments, the offline analysis server 17 and the speech-to-text processor 18 are included in the relationship determination system 10.

Figure 3:
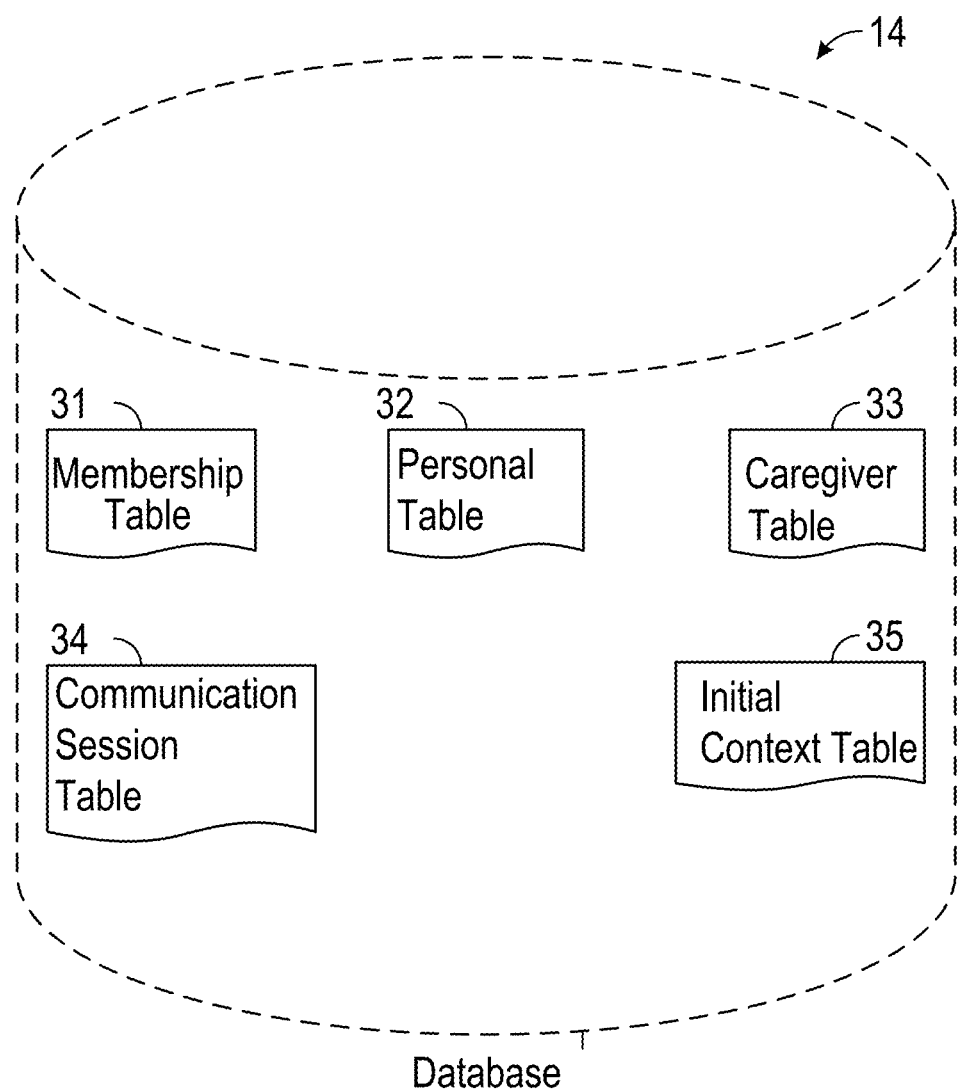
FIG. 3 is a schematic diagram illustrating data which may be stored in the database of the relationship determination system, according to various exemplary embodiments.

FIG. 3 is a schematic diagram illustrating data that is stored in the database 14 of the relationship determination system 10, according to certain exemplary embodiments. While the content of the database 14 is shown to comprise a number of tables, the data could be stored in other types of data structures (e.g., as an object-oriented database).

The database 14 includes a membership table 31, a personal table 32, a caregiver table 33, a communication session table 34, and an initial context table 35.

The membership table 31 stores membership data that includes general membership data related to the organization, rules implemented by the organization for membership, member authentication requirements, etc. The membership data can be for example data required for authentication, specific call routing requirements, information on member benefits, information on the member's plan, etc.

The personal table 32 stores personal data related to all the members associated with the organization providing the customer service. The personal data can also be related to all other patients associated with the organization via the members. The personal table 32 can also include a personal graph that stores information regarding relationships and associations between members and other patients.

The caregiver table 33 stores caregiver data including rules applied by the organization to authenticate caregivers, identification data for each of the caregivers in the system and the patients each caregiver is associated with, etc. Caregiver data can be, for example, types of permissible data used to authenticate a person as a caregiver such as pin numbers, member numbers, etc. Caregiver data can also set the types of data to be obtained from the user to validate the caregiver relationship.

The communication session table 34 stores communication session data which is data related to a communication session between the agent client device 11 and the member-related client device 12. Communication session data can be, for example, Automatic Number Identification (ANI), Dialed Number Identification Service (DNIS), Membership Information provided (e.g., Prescription number, Membership number), authentication status (e.g., partial or complete). Communication session data can also be an indication of whether a particular member or members have been authenticated, whether a member was directly authenticated as a caregiver, etc. Communication session data can also be, for example, transcribed text of full utterances provided by the user.

The initial context table 35 stores initial context data related to the member (e.g., user or patient) that has established a communication session with the agent client device 12. Initial context data can include, for example, website login information, automatic number identifier, telephone number. Initial context data can also include member account information such as name, address, employer, medication, insurance information, preferred pharmacy, and information on member's spouse or dependents.

Although the following flow diagrams may describe the operations as a sequential process, many of the operations can be performed in parallel or concurrently. In addition, the order of the operations may be re-arranged. A process is terminated when its operations are completed. A process may correspond to a method, a procedure, etc. The steps of methods may be performed in whole or in part, may be performed in conjunction with some or all of the steps in other methods, and may be performed by any number of different systems, such as the systems 1, 700 described in FIG. 1 and/or FIG. 7.

Figure 4:
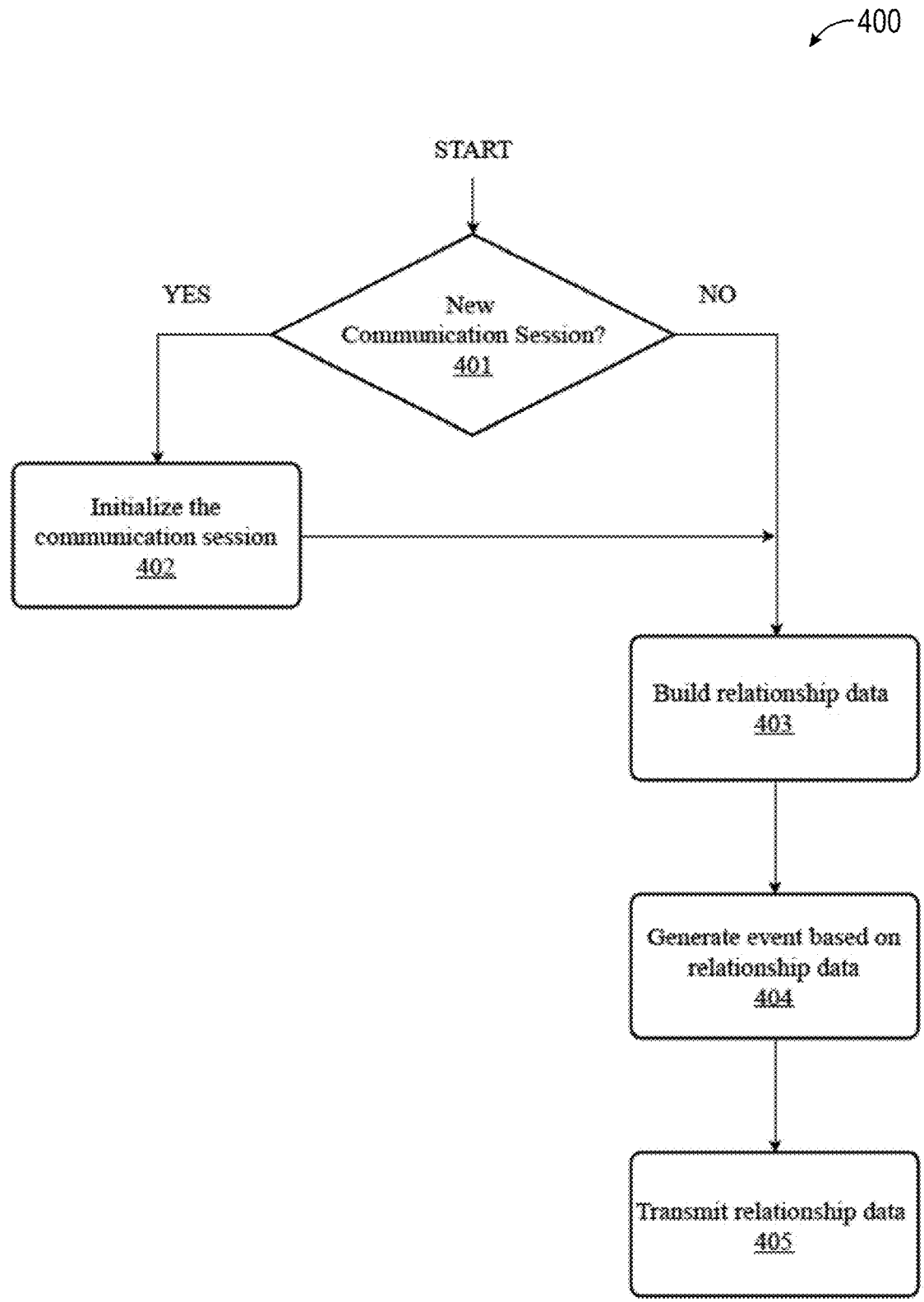
FIG. 4 is a flow diagram of an exemplary method determining a relationship according to various aspects of the disclosure.

FIG. 4 is a flow diagram of an exemplary method 400 determining a relationship according to various aspects of the disclosure. The method 400 can be performed by the relationship determination system 10 in FIG. 1. In one embodiment, a processor included in the relationship determination system 10 performs the method 400 or causes the relationship determination system 10 to perform the method 400.

Method 400 starts, at operation 401, with a processor determining whether a new communication session is being established between the agent client device 11 and the member-related client device 12. The communication session can include, for example, an interactive voice response (IVR), a voice call, or an electronic message.

When the processor determines that a new communication session is being established at operation 401, the processor initializes the communication session between the agent client device 11 and the member-related client device 12 at operation 402. Initializing the communication session at operation 402 can include retrieving initial context data of the member and storing the initial context data of the member in the database 14. In one embodiment, the initial context data can include, for example, a website login information, an automatic number identifier (AIN), or telephone number. The initial context data can also include, for example, a member account information that includes name, address, employer, medication, insurance information, preferred pharmacy, or information on member's spouse or dependents.

When the processor determines that the communication session being established is not new (e.g., a continuation of a prior established communication session) at operation 401 or when the processor completes the initialization of the communication session at operation 402, the processor builds relationship data at operation 403. At operation 404, the processor generates an event based on the relationship data. In one embodiment, the event includes the pertinent information about the type of relationship that is detected based on the relationship data. For example, the pertinent information can be "parent of member (identification number) 123 and member 123 is a minor". In one embodiment, a plurality of events can be generated at operation 404 because a user can be calling about several different members during a given call. A separate event can be generated at operation 404 as the context changes. For example, a user can be a user who is calling to fill a prescription for his wife and then his daughter. In this example, two separate events can be generated: a first event for husband and wife and a second event for father and daughter. At operation 405, the processor transmits the relationship data to the agent client device 11. In one embodiment, the processor causes the relationship data to be displayed or otherwise output by the agent client device 11 on an interface coupled to or included in the agent client device 11.

Figure 5:
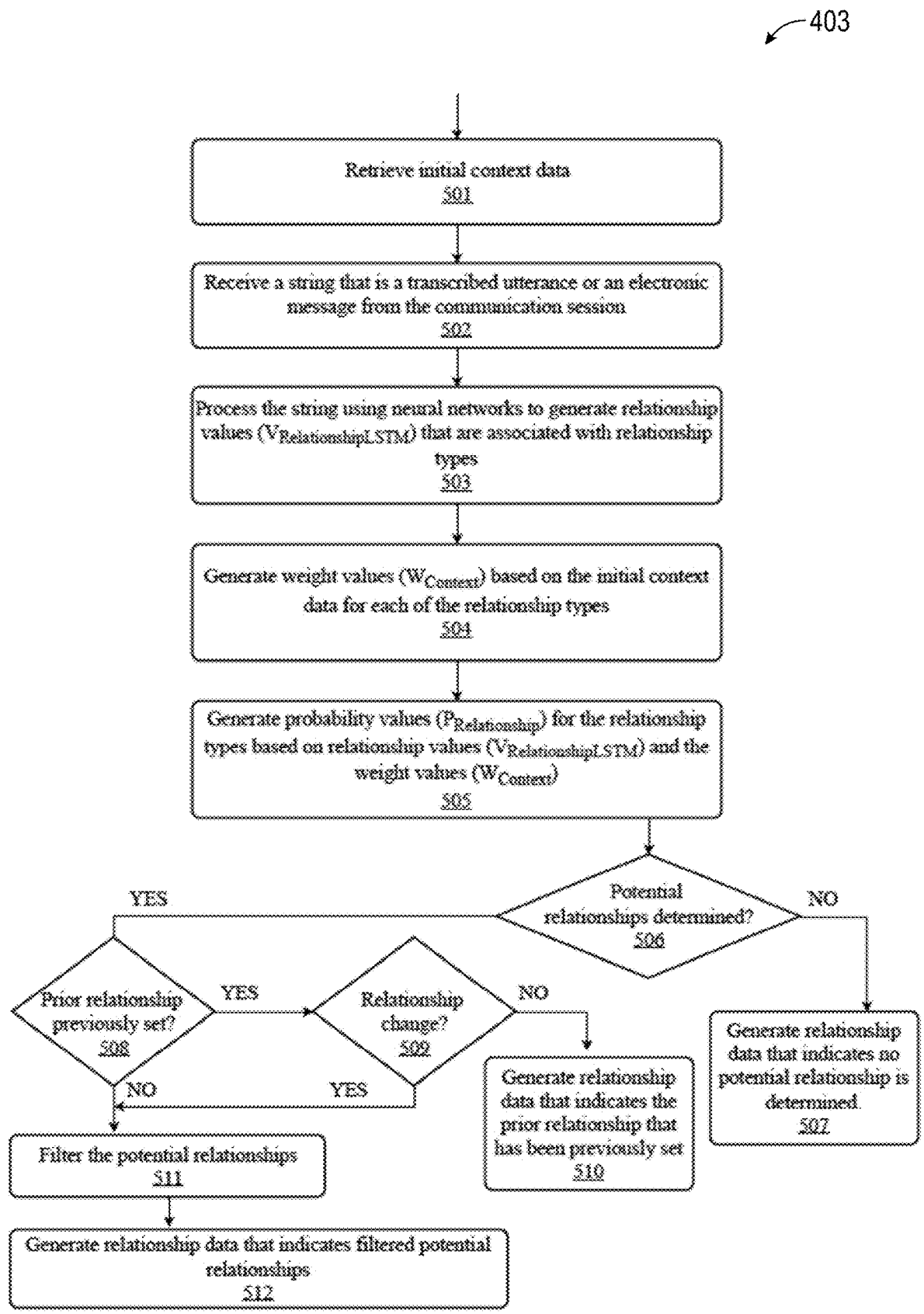
FIG. 5 is a flow diagram of an exemplary method of building relationship data (operation 403) in the method of determining a relationship from FIG. 4 according to various aspects of the present disclosure.

FIG. 5 is a flow diagram of an exemplary method of building relationship data (operation 403) in the method of determining a relationship from FIG. 4 according to various aspects of the present disclosure. Since the user may be communicating with the agent client device 11 on behalf of another person (e.g., a patient, a member, or both), the method of building relationship data is performed to determine and indicate to the agent the relationship between the user and the patient in order further facilitate the agent in assisting the user. The method 400 can be performed by the relationship determination system 10 in FIG. 1. In one embodiment, a processor included in the relationship determination system 10 performs the method 400 or causes the relationship determination system 10 to perform the method 400.

At operation 501, the processor retrieves initial context data of the member associated with the member-related client device 12 from the database 14.

At operation 502, the processor receives a string that is a transcribed or digitized utterance or an electronic message from the communication session. When the communication session includes audio call, portions of the audio call (e.g., the utterance) are converted from speech to text to generate the string in real time, e.g., using a speech-to-text processor 18 (FIG. 2). For example, a string can be an array of characters that contains the data from the automated transcription. The string can include one or more words that was provided by the user in response to a query. The string can also include a series of singularly spoken letters or number. For example, the user may be providing a member identification number or a prescription number. The string can also include a combination of words and singularly spoken letters or numbers. To generate the strings, the speech-to-text processor 18 can implement Fast Fourier Transforms (FFTs) or Neural Networks such as Long-Short Term Memory Neural Networks (LSTM). In one embodiment, the string that is an electronic message can be a portion of an online chat exchanged between the agent and the member that is received by the processor in real time. In this embodiment, the processor generates strings by processing online chat to parse and separate the different portions of the online chat.

To determine the potential relationships between the member and the patient, at operation 503, the processor processes the string using neural networks to generate relationship values ($V_{RelationshipLSTM}$) that are associated with relationship types. Each of the neural networks can be Long Short-Term Memory (LSTM) neural networks. In one embodiment, each Long-Short Term Memory Neural Networks (LSTM) neural network processes the string at an input layer, an embed layer, an LSTM layer and a Sigmoid layer. The input layer receives the string and separate the string into separate words. Each word is passed to a subsequent layer for processing. For example, the embed layer receives and translates each word into numerical values. The LSTM layer generates a value for each word but the value generated for the first word is carried over to the analysis of the second word. The LSTM layer creates a semantic understanding of the relationship given that there is a memory of the analysis of each word that is carried over. This allows the neural network to assess a whole string more accurately by virtue of having context. The Sigmoid layer is the final layer that receives the words for processing and outputs the relationship values. In an example embodiment, the neural networks can include a Gated Recurrent Unit (GRU) neural network.

The relationship values that are generated using the neural networks can be a value between 0 and 1, wherein 0 indicates a lower likelihood of the relationship type and wherein 1 indicates a higher likelihood of the relationship type. For example, the relationship types include a parent-child relationship in which the user is a parent (who may or not be a member) and the patient is the member's child (who is a member); child-parent relationship in which the user is a caretaker child and the patient is the member and parent; spousal relationship in which the user and the patient are spouses, with at least the patient being a member; professional caregiver relationship in which the user is a professional caregiver for the patient, who is the member; and a medical professional-patient relationship in which the user is a medical professional and the patient is the member. Each of the relationship types is allocated one neural network that is trained offline (e.g., using the offline analysis server 17) to assess whether the string indicates the relationship type to which it is allocated. For example, a first neural network is trained to assess whether the string indicates a parent-child relationship, a second neural network is trained to assess whether the string indicates a child-parent relationship, a third neural network is trained to assess whether the string indicates a spousal relationship, a fourth neural network is trained to assess whether the string indicates a professional caregiver relationship, a fifth neural network is trained to assess whether the string indicates a medical professional relationship.

In an example embodiment, the first neural network may learn that a string such as "my child," "my daughter," "my son," "my kid" or use of the child's name, which is stored in the database 14, increases the likelihood that there is a parent-child relationship.

In an example embodiment, the second neural network may learn that a string such as "my parent," "my dad," "my mom," "my father," "my mother," or the use of the parent's name, which is stored in the database 14, increases the likelihood that there is a child-child relationship.

At operation 504, the processor generates weight values ($W_{Context}$) based on the initial context data of the member for each of the relationship types. The weight values are dynamically generated when the initial context data for the member is updated. The initial context data can be updated in real-time based on, for example, information obtained from the processing of the string in operation 503, changes in data stored in the database 14, etc. The weight values that are based on the initial context data of the member are used to add further accuracy to the determination of potential relationships between the user and the patient. For example, if the initial context data includes the information that the member has no children as dependents, the weight value generated for a parent-child relationship will be a lower value to indicate that the parent-child relationship is not likely relative to the initial context data indicating that the member has children. For example, if the initial context data includes the information that the member's parents are deceased, the weight value generated for a child-relationship relationship will be a lower value to indicate that the child-parent relationship is not likely relative to the initial context data indicating that the member's parents are alive. For example, if the initial context data includes the information that the member is married, the weight value generated for a spousal relationship will be a higher value to indicate that the spousal relationship is likely relative to initial context data indicating that the member is single. For example, if the initial context data includes the information that the member has a caregiver, the weight value generated for a caregiver relationship will be a higher value to indicate that the caregiver relationship is likely relative to initial context data indicating that the member does not have a caregiver. For example, if the initial context data includes the information that the member uses a specific medical professional, the weight value generated for a medical professional relationship will be a higher value to indicate that the medical professional relationship is likely relative to initial context data indicating that the member does not use that medical professional.

In one embodiment, weight values ($W_{Context}$) can be obtained using an evolutionary algorithm during a training process according to the following equation:

$$W_{Context} = W_{Relationship} * \tan h(Count_{Relationship}/Count_{TotalRelationships})$$

In this equation, the weight value ($W_{Context}$) is based on the weight of a type of relationship (e.g., parent/child), the total count of that type of relationship ($Count_{Realationship}$) and the total count of all possible types of relationships ($Count_{TotalRelationships}$).

At operation 505, the processor generates probability values ($P_{Relationship}$) for the relationship types based on relationship values ($V_{RelationshipLSTM}$) and the weight values ($W_{Context}$). For example, the processor can generate the probability values as follows:

$$P_{Relationship} = W_{Context} * V_{RelationshipLSTM}$$

In this embodiment, a probability value for each of the relationship types is generated. The probability value indicates the probability that the relationship type is representative of the relationship between the user and the patient, who can be the member. For example, the probability value for a parent-child relationship (e.g., $P_{Reationship}$(parent-child)) is generated by multiplying the weight value associated with the parent-child relationship (e.g., $W_{context}$(parent-child))) by the relationship value associated with the parent-child relationship (e.g., $V_{RelationshipLSTM}$(parent-child)).

At operation 506, the processor determines, based on the probability values, whether any potential relationships are identified. When the probability values are lower than a threshold, the processor determines that no potential relationships are determined, and at operation 507, the processor generates the relationship data that indicates that no potential relationships are determined.

When at least one of the probability values is higher than the threshold, the processor determines that potential relationships are identified, and at operation 508, the processor determines if a prior relationship between the user and the patient has previously been set during the communication session. For example, a prior relationship can previously have been set based on an earlier string related to an earlier utterance or earlier electronic message during the same communication session. If the processor determines that no prior relationship has been set, the processor continues to operation 511.

If the processor determines that a prior relationship has previously been set at operation 508, the processor determines if the potential relationship indicates that there is a change in the prior relationship that has previously been set during the communication session at operation 509. For example, at the beginning of the communication session, the user is determined to be talking about his daughter such that the relationship data associated with the relationship between the member and the patient indicates a parent-child relationship. At a later time in the communication session, the user is still talking about his daughter such that the processing of the string "my daughter's prescription" and the weight value indicates a potential relationship that is a parent-child relationship. In this example, the processor determines that there is no change in the prior relationship that has been previously been set. When the processor determines that there is no change at operation 509, the processor generates a relationship data that indicates the prior relationship that has previously been set at operation 510 and the relationship remains valid.

In contrast, at a later time in the communication session, if the user is talking about his wife such that the processing of the string (e.g., "my wife's prescription") and the weight value indicate a potential relationship that is a spousal relationship. Accordingly, in this example, the potential relationships may not include a parent-child relationship such that the processor can determine at operation 509 that there is a change in the prior relationship that has previously been set during the communication session. When the processor determines at operation 509 that there is a change, the processor continues to operation 511.

At operation 511, the processor filters the potential relationships in an effort to further increase accuracy. The processor can filter the potential relationships to remove one or more of the potential relationships that are determined to be less likely than the other potential relationships. The filtering can narrow the potential relationships to those known or predicted to be possible for a user. The processor can filter the potential relationships by identifying additional context from the string using natural language processing (NLP). For example, additional context can include for example drug names, prescription numbers, medication identifiers, etc. The processor can also filter the potential relationships by building a model of the patient by retrieving data from database that includes, for example, patient information from the database, caregiver information from the database, etc. The processor can further filter the potential relationships by using relationship business rules. The relationship business rules can include rules stored in the database regarding the membership, the member, the patient, etc. For example, based on the relationship business rules, the processor can identify if a user is set up to be a caregiver, identify the user's phone number, identify using the membership that is set up whether there are adult children, minor children, or a spouse on the membership plan. At operation 512, the processor generates relationship data that indicates the filtered potential relationships.

Figure 6:
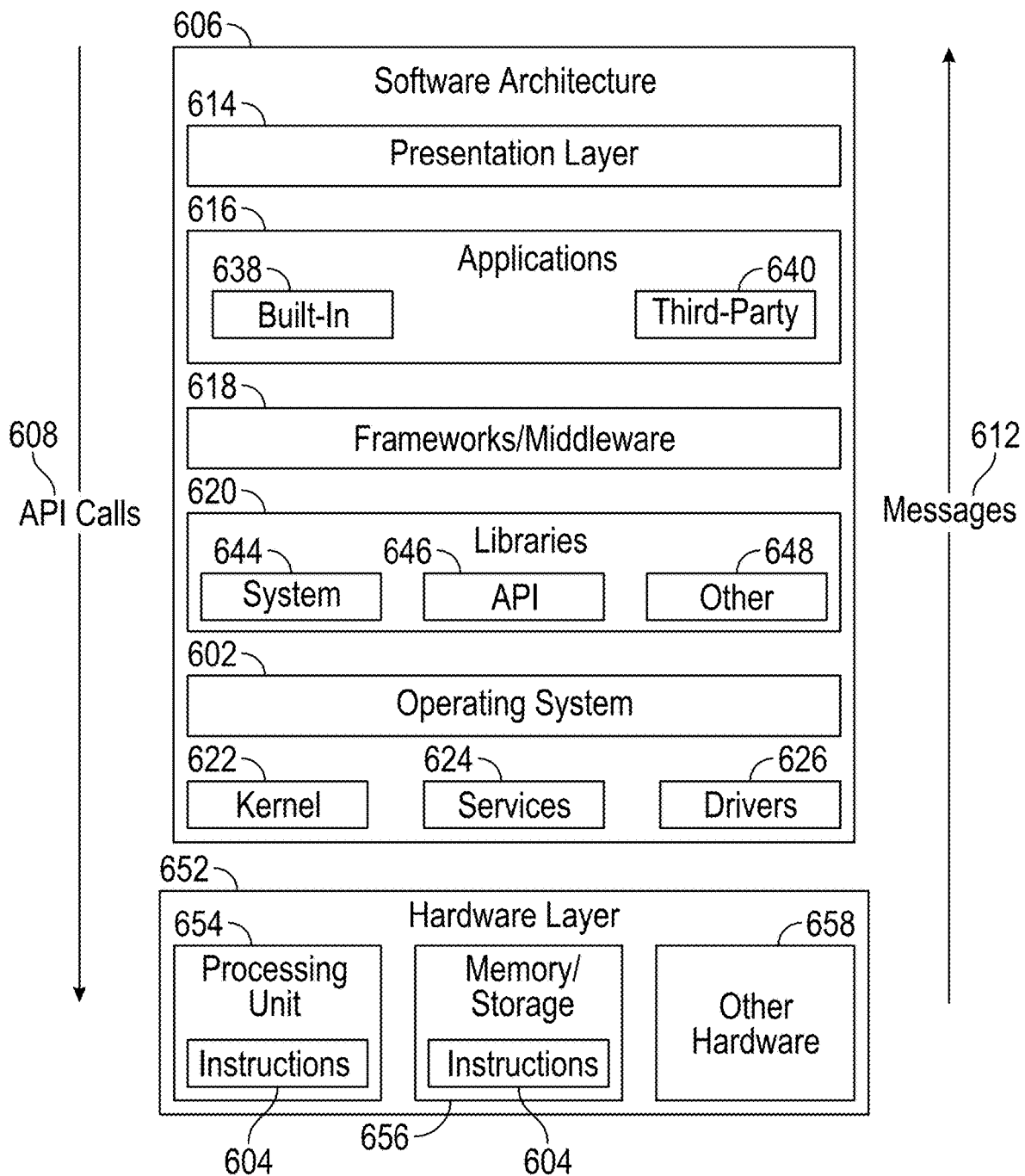
FIG. 6 is a block diagram illustrating a representative software architecture, which may be used in conjunction with various hardware architectures herein described.

FIG. 6 is a block diagram illustrating an exemplary software architecture 606, which may be used in conjunction with various hardware architectures herein described. FIG. 6 is a non-limiting example of a software architecture and it will be appreciated that many other architectures may be implemented to facilitate the functionality described herein. The software architecture 606 may execute on hardware such as machine 700 of FIG. 7 that includes, among other things, processors 704, memory 714, and I/O components 718. A representative hardware layer 652 is illustrated and can represent, for example, the machine 700 of FIG. 7. The representative hardware layer 652 includes a processing unit 654 having associated executable instructions 604. Executable instructions 604 represent the executable instructions of the software architecture 606, including implementation of the methods, components and so forth described herein. The hardware layer 652 also includes memory or storage modules memory/storage 656, which also have executable instructions 604. The hardware layer 652 may also comprise other hardware 658.

As used herein, the term "component" may refer to a device, physical entity or logic having boundaries defined by function or subroutine calls, branch points, application program interfaces (APIs), or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions.

Components may constitute either software components (e.g., code embodied on a machine-readable medium) or hardware components. A "hardware component" is a tangible unit capable of performing certain operations and may be configured or arranged in a certain physical manner. In various exemplary embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations.

A hardware component may be a special-purpose processor, such as a Field-Programmable Gate Array (FPGA) or an Application Specific Integrated Circuit (ASIC). A hardware component may also include programmable logic or circuitry that is temporarily configured by software to perform certain operations. For example, a hardware component may include software executed by a processor or other programmable processor. Once configured by such software, hardware components become specific machines (or specific components of a machine) uniquely tailored to perform the configured functions and are no longer processors. It will be appreciated that the decision to implement a hardware component mechanically, in dedicated and permanently configured circuitry, or in temporarily configured circuitry (e.g., configured by software) may be driven by cost and time considerations.

A processor may be, or in include, any circuit, circuitry, or virtual circuit (a physical circuit emulated by logic executing on an actual processor) that manipulates data values according to control signals (e.g., "commands", "op codes", "machine code", etc.) and which produces corresponding output signals that are applied to operate a machine. A processor may, for example, be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC) or any combination thereof. A processor may further be a multi-core processor having two or more independent processors (sometimes referred to as "cores") that may execute instructions contemporaneously. The processor as used herein may be a hardware component, which is in at least one of the devices, systems, servers and the like. The processor may include multiple cores and may be spread across multiple devices. The processor includes circuitry to execute instructions relating to the methods and structures described herein for determining relationships and outputting relationship data that is used by various device and their users.

Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a processor configured by software to become a special-purpose processor, the processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access.

For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components.

Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)). The performance of certain of the operations may be distributed among the processors, not only residing within a single machine, but deployed across a number of machines. In some exemplary embodiments, the processors or processor-implemented components may be located in a single geographic location (e.g., within a home environment, an office environment, or a server farm). In other exemplary embodiments, the processors or processor-implemented components may be distributed across a number of geographic locations.

In the exemplary architecture of FIG. 6, the software architecture 606 may be conceptualized as a stack of layers where each layer provides particular functionality. For example, the software architecture 606 may include layers such as an operating system 602, libraries 620, applications 616 and a presentation layer 614. Operationally, the applications 616 or other components within the layers may invoke application programming interface (API) API calls 608 through the software stack and receive messages 612 in response to the API calls 608. The layers illustrated are representative in nature and not all software architectures have all layers. For example, some mobile or special purpose operating systems may not provide a frameworks/middleware 618, while others may provide such a layer. Other software architectures may include additional or different layers.

The operating system 602 may manage hardware resources and provide common services. The operating system 602 may include, for example, a kernel 622, services 624 and drivers 626. The kernel 622 may act as an abstraction layer between the hardware and the other software layers. For example, the kernel 622 may be responsible for memory management, processor management (e.g., scheduling), component management, networking, security settings, and so on. The services 624 may provide other common services for the other software layers. The drivers 626 are responsible for controlling or interfacing with the underlying hardware. For instance, the drivers 626 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 620 provide a common infrastructure that is used by the applications 616 or other components or layers. The libraries 620 provide functionality that allows other software components to perform tasks in an easier fashion than to interface directly with the underlying operating system 602 functionality (e.g., kernel 622, services 624 or drivers 626). The libraries 620 may include system libraries 644 (e.g., C standard library) that may provide functions such as memory allocation functions, string manipulation functions, mathematical functions, and the like. In addition, the libraries 620 may include API libraries 646 such as media libraries (e.g., libraries to support presentation and manipulation of various media format such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 620 may also include a wide variety of other libraries 648 to provide many other APIs to the applications 616 and other software components/modules.

The frameworks/middleware 618 (also sometimes referred to as middleware) provide a higher-level common infrastructure that may be used by the applications 616 or other software components/modules. For example, the frameworks/middleware 618 may provide various graphic user interface (GUI) functions, high-level resource management, high-level location services, and so forth. The frameworks/middleware 618 may provide a broad spectrum of other APIs that may be utilized by the applications 616 or other software components/modules, some of which may be specific to a particular operating system 602 or platform.

The applications 616 may use built in operating system functions (e.g., kernel 622, services 624 or drivers 626), libraries 620, and frameworks/middleware 618 to create user interfaces to interact with users of the system. Alternatively, or additionally, in some systems interactions with a user may occur through a presentation layer, such as presentation layer 614. In these systems, the application/component "logic" can be separated from the aspects of the application/component that interact with a user.

Figure 7:
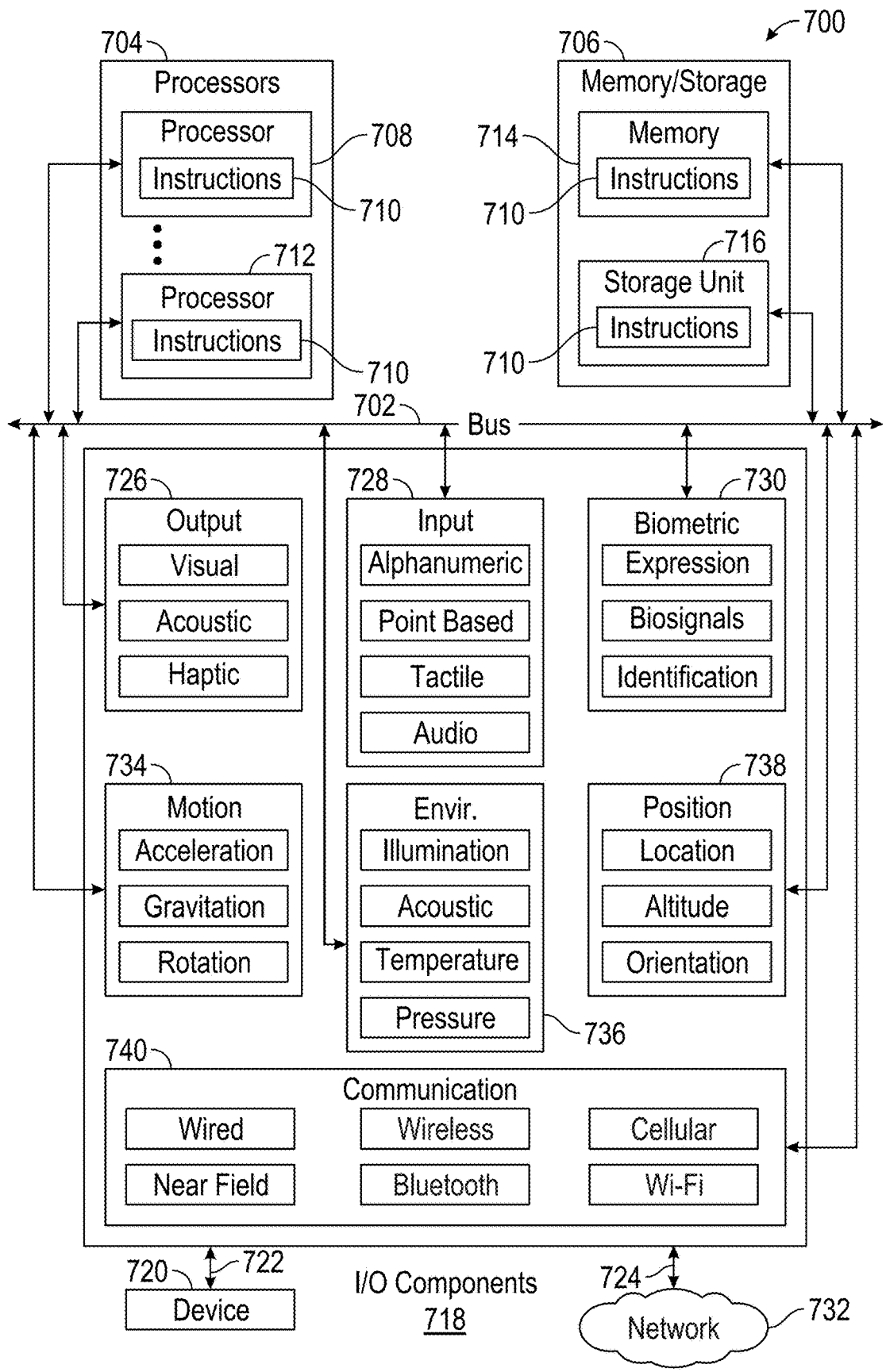
FIG. 7 is a block diagram illustrating components of a machine, according to some exemplary embodiments, able to read instructions from a machine-readable medium (e.g., a machine-readable storage medium) and perform any one or more of the methodologies discussed herein.

FIG. 7 is a block diagram illustrating components (also referred to herein as "modules") of a machine 700, according to some exemplary embodiments, able to read instructions from a machine-readable medium (e.g., a machine-readable storage medium) and perform any one or more of the methodologies discussed herein. Specifically, FIG. 7 shows a diagrammatic representation of the machine 700 in the example form of a computer system, within which instructions 710 (e.g., software, a program, an application, an applet, an app, or other executable code) for causing the machine 700 to perform any one or more of the methodologies discussed herein may be executed. As such, the instructions 710 may be used to implement modules or components described herein. The instructions 1010 transform the non-programmed machine 700 into a particular machine 700 programmed to carry out the described and illustrated functions in the manner described. In alternative embodiments, the machine 700 operates as a standalone device or may be coupled (e.g., networked) to other machines. In a networked deployment, the machine 700 may operate in the capacity of a server machine or a client machine in a server-client network environment, or as a peer machine in a peer-to-peer (or distributed) network environment. The machine 700 may comprise, but not be limited to, a server computer, a client computer, a personal computer (PC), a laptop computer, a network router, a network switch, a network bridge, or any machine capable of executing the instructions 710, sequentially or otherwise, that specify actions to be taken by machine 700. Further, while only a single machine 700 is illustrated, the term "machine" shall also be taken to include a collection of machines that individually or jointly execute the instructions 710 to perform any one or more of the methodologies discussed herein.

The machine 700 may include processors 704, memory memory/storage 706, and I/O components 718, which may be configured to communicate with each other such as via a bus 702. The memory/storage 706 may include a memory 714, such as a main memory, or other memory storage, and a storage unit 716, both accessible to the processors 704 such as via the bus 702. The storage unit 716 and memory 714 store the instructions 710 embodying any one or more of the methodologies or functions described herein. The instructions 710 may also reside, completely or partially, within the memory 714, within the storage unit 716, within at least one of the processors 704 (e.g., within the processor's cache memory), or any suitable combination thereof, during execution thereof by the machine 700. Accordingly, the memory 714, the storage unit 716, and the memory of processors 704 are examples of machine-readable media.

As used herein, the term "machine-readable medium," "computer-readable medium," or the like may refer to any component, device or other tangible media able to store instructions and data temporarily or permanently. Examples of such media may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) or any suitable combination thereof. The term "machine-readable medium" should be taken to include a single medium or multiple media (e.g., a centralized or distributed database, or associated caches and servers) able to store instructions. The term "machine-readable medium" may also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" may refer to a single storage apparatus or device, as well as "cloud-based" storage systems or storage networks that include multiple storage apparatus or devices. The term "machine-readable medium" excludes signals per se.

The I/O components 718 may include a wide variety of components to provide a user interface for receiving input, providing output, producing output, transmitting information, exchanging information, capturing measurements, and so on. The specific I/O components 718 that are included in the user interface of a particular machine 700 will depend on the type of machine. It will be appreciated that the I/O components 718 may include many other components that are not shown in FIG. 7. The I/O components 718 are grouped according to functionality merely for simplifying the following discussion and the grouping is in no way limiting. In various exemplary embodiments, the I/O components 718 may include output components 726 and input components 728. The output components 726 may include visual components (e.g., a display such as a plasma display panel (PDP), a light emitting diode (LED) display, a liquid crystal display (LCD), a projector, or a cathode ray tube (CRT)), acoustic components (e.g., speakers), other signal generators, and so forth. The input components 728 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location or force of touches or touch gestures, or other tactile input components), audio input components (e.g., a microphone), and the like. The input components 728 may also include one or more image-capturing devices, such as a digital camera for generating digital images or video.

In further exemplary embodiments, the I/O components 718 may include biometric components 730, motion components 734, environmental environment components 736, or position components 738, as well as a wide array of other components. One or more of such components (or portions thereof) may collectively be referred to herein as a "sensor component" or "sensor" for collecting various data related to the machine 700, the environment of the machine 700, a user of the machine 700, or a combinations thereof.

Communication may be implemented using a wide variety of technologies. The I/O components 718 may include communication components 740 operable to couple the machine 700 to a network 732 or devices 720 via coupling 722 and coupling 724 respectively. For example, the communication components 740 may include a network interface component or other suitable device to interface with the network 732. In further examples, communication components 740 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 720 may be another machine or any of a wide variety of peripheral devices (e.g., a peripheral device coupled via a Universal Serial Bus (USB)). Moreover, the communication components 740 may detect identifiers or include components operable to detect identifiers.

Where a phrase similar to "at least one of A, B, or C," "at least one of A, B, and C," "one or more A, B, or C," or "one or more of A, B, and C" is used, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A method, comprising:
retrieving, by a processor, initial context data of a user associated with a member-related client device from a database, wherein a communication session is created between the member-related client device and an agent client device;
receiving an array data structure that is a transcribed utterance or an electronic message from the communication session;
determining a plurality of potential relationships between the user and a patient that is the subject of the array data structure, wherein determining the plurality of potential relationships includes:
generating a plurality of relationship values associated with a plurality of relationship types, based on the array data structure;
generating a plurality of weight values based on the initial context data of the user for each of the plurality of relationship types;
generating a plurality of probability values for the plurality of relationship types, based on the plurality of relationship values and the plurality of weight values; and
identifying the plurality of potential relationships, based on the plurality of probability values;
filtering the plurality of potential relationships to generate filtered potential relationships;
generating relationship data that includes the filtered potential relationships; and
causing the relationship data to be displayed by the agent client device.

2. The method of claim 1, wherein the communication session includes an interactive voice response (IVR) or a voice call; and
wherein the transcribed utterance is based on a speech to text conversion of a portion of the IVR or the voice call.

3. The method of claim 1, further comprising:
initializing a communication session between the member-related client device and the agent client device, wherein initializing the communication session includes:
retrieving the initial context data of the user, wherein the initial context information including at least one of: website login information, automatic number identifier, or telephone number; and
storing the initial context data of the user in the database.

4. The method of claim 1, wherein the initial context data of the user includes member account information including name, address, employer, medication, insurance information, preferred pharmacy, or information on user's spouse or dependents.

5. The method of claim 1, wherein filtering the plurality of potential relationships includes at least one of:
identifying additional context from the array data structure using natural language processing (NLP); or
building a model of the patient by using patient information from the database and caregiver information from the database.

6. The method of claim 1, wherein filtering the plurality of potential relationships further comprises:
comparing the plurality of probability values to a threshold; and
when the plurality of probability values is lower than the threshold,
determining no potential relationships between the user and the patient; and
wherein generating the relationship data further comprises generating an indication of no determined potential relationships.

7. The method of claim 1, further comprising:
determining that a prior relationship between the user and the patient has previously been set during the communication session, based on an earlier array data structure that is an earlier transcribed utterance or an earlier electronic message from the communication session; and
when no change to the prior relationship is indicated by the plurality of potential relationships,
generating the relationship data to indicate validity of the prior relationship set during the communication session.

8. A system comprising:
a processor; and
a memory component having instructions stored thereon, which, when executed by the processor, cause the processor to perform operations comprising:
retrieving initial context data of a user associated with a member-related client device from a database, wherein a communication session is created between the member-related client device and an agent client device;
obtaining an array data structure that is a transcribed utterance or an electronic message from the communication session;
determining a plurality of potential relationships between the user and a patient that is the subject of the array data structure, wherein determining the plurality of potential relationships includes:
generating a plurality of relationship values associated with a plurality of relationship types, based on the array data structure;
generating a plurality of weight values based on the initial context data of the user for each of the plurality of relationship types;
generating a plurality of probability values for the plurality of relationship types based on the plurality of relationship values and the plurality of weight values; and
identifying the plurality of potential relationships, based on the plurality of probability values;
filtering the plurality of potential relationships to generate filtered potential relationships;
generating relationship data that includes the filtered potential relationships; and
causing the relationship data to be displayed by the agent client device.

9. The system of claim 8, further comprising:
a set of communication components communicatively coupled to the processor and the memory component, the set of communication components operable to:
interface with at least one network; and
transmit and receive data via the at least one network;
wherein the operations further comprise:
transmitting the relationship data including the filtered potential relationships to the agent client device via the set of communication components.

10. The system of claim 8, wherein the operations further comprise:
detecting an update to the initial context data based on a change to the database; and
in response to the update,
dynamically generating the plurality of weight values.

11. The system of claim 8, wherein obtaining the array data structure further comprises:
converting at least one portion of an audio call from speech to text to generate the array data structure that is the transcribed utterance from the communication session, wherein the communication session comprises the audio call; and
wherein the operations further comprise:
processing the array data structure using neural networks to generate the plurality of relationship values.

12. The system of claim 11, wherein the operations further comprise:
processing a string data structure using one or more Long-Short Term Memory (LSTM) neural networks, wherein the array data structure comprises the string data structure, and wherein the neural networks comprise the one or more LSTM neural networks;
generating the plurality of relationship values, based on processing the string data structure using the one or more LSTM neural networks; and
generating the plurality of probability values for the plurality of relationship types, based on the relationship values generated by processing the string data structure using the one or more LSTM neural networks.

13. The system of claim 8, wherein the operations further comprise:
processing the electronic message to parse and separate portions of the electronic message into a plurality of array data structures including the array data structure, wherein the electronic message comprises an online chat message or a text message;
processing the array data structure using neural networks to generate the plurality of relationship values.

14. The system of claim 13, wherein the operations further comprise:
processing a string data structure using one or more Long-Short Term Memory (LSTM) neural networks, wherein the array data structure comprises the string data structure, and wherein the neural networks comprise the one or more LSTM neural networks;
generating the plurality of relationship values, based on processing the string data structure using the one or more LSTM neural networks; and
generating the plurality of probability values for the plurality of relationship types, based on the relationship values generated by processing the string data structure using the one or more LSTM neural networks.

15. A method, comprising:
during a communication session between a user and an agent of an organization,
performing an analysis of communications exchanged between a member-related client device operated by the user and an agent client device operated by the agent, by:
obtaining an array data structure based on a transcribed utterance or an electronic message from the communication session;
determining a plurality of potential relationships between the user and a member of the organization, using the array data structure; and
filtering the plurality of potential relationships to generate filtered potential relationships;
generating relationship data based on at least the filtered potential relationships; and
transmitting the relationship data to the agent client device for display on the agent client device.

16. The method of claim 15, further comprising:
identifying establishment of the communication session between the agent client device and the member-related client device, wherein the communication session comprises an interactive voice response (IVR), a voice call, or an electronic message; and
in response to identifying the establishment of the communication session,
initializing the communication session using initial context data of the member, to create an initialized communication session; and
performing the analysis based on the initialized communication session.

17. The method of claim 16, wherein initializing the communication session further comprises:
retrieving the initial context data of the member from the member-related client device, wherein the initial context data comprises at least one of a website login information, an automatic number identifier (ANI), or a telephone number;
identifying the member based on the initial context data; and
storing the initial context data.

18. The method of claim 15, wherein performing the analysis further comprises:
identifying a previously set prior relationship between the user and the member; and
wherein the method further comprises:
generating the relationship data based on the filtered potential relationships and the previously set prior relationship, to include an indication of validity of the previously set prior relationship.

19. The method of claim 15, further comprising:
generating an event indicating a relationship type associated with the user and the member, based on the relationship data; and
in response to the event, transmitting the relationship data to the agent client device.

20. The method of claim 15, further comprising:
during the communication session, determining a context change indicating a second member associated with the user;
generating a plurality of events, based on the context change, by:
generating a first event indicating at least a first relationship type associated with the user and the member, based on the relationship data; and
generating a second event indicating a second relationship type associated with the user and the second member, based on the relationship data;
wherein the plurality of events includes at least the first event and the second event; and
in response to the first event, transmitting the relationship data including the first relationship type associated with the user and the member; and
in response to the second event, transmitting the relationship data including the second relationship type associated with the user and the second member.

* * * * *